United States Patent
Manoux et al.

(10) Patent No.: US 8,365,975 B1
(45) Date of Patent: Feb. 5, 2013

(54) CAM-CONTROLLED KNIFE FOR SURGICAL INSTRUMENT

(75) Inventors: Philipe R. Manoux, Oakland, CA (US); Michael P. Schaller, Palo Alto, CA (US)

(73) Assignee: Cardica, Inc., Redwood City, CA (US)

( * ) Notice: Subject to any disclaimer, the term of this patent is extended or adjusted under 35 U.S.C. 154(b) by 222 days.

(21) Appl. No.: 12/772,322

(22) Filed: May 3, 2010

Related U.S. Application Data

(60) Provisional application No. 61/175,786, filed on May 5, 2009.

(51) Int. Cl.
*A61B 17/068* (2006.01)

(52) U.S. Cl. ........... 227/180.1; 227/19; 227/176.1; 606/139; 606/21

(58) Field of Classification Search ......... 227/180.1, 227/176.1, 19, 175.2; 606/139, 219
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,675,688 A | 7/1972 | Bryan et al. |
| 3,899,914 A | 8/1975 | Akiyama |
| 3,955,581 A | 5/1976 | Spasiano et al. |
| 4,086,926 A | 5/1978 | Green et al. |
| 4,228,895 A | 10/1980 | Larkin |
| 4,275,813 A | 6/1981 | Noiles |
| 4,475,679 A | 10/1984 | Fleury, Jr. |
| 4,633,861 A | 1/1987 | Chow et al. |
| 4,655,222 A | 4/1987 | Florez et al. |
| 4,719,917 A | 1/1988 | Barrows et al. |
| 4,762,260 A | 8/1988 | Richards et al. |
| 4,969,591 A | 11/1990 | Richards et al. |
| 4,978,049 A | 12/1990 | Green |
| 5,156,315 A | 10/1992 | Green et al. |
| 5,170,925 A | 12/1992 | Madden et al. |
| 5,192,288 A | 3/1993 | Thompson et al. |
| 5,307,976 A | 5/1994 | Olson et al. |
| 5,413,272 A | 5/1995 | Green et al. |
| 5,476,206 A | 12/1995 | Green et al. |
| 5,547,117 A | 8/1996 | Hamblin et al. |
| 5,553,765 A | 9/1996 | Knodel et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory 39* (2004), (Nov. 2004),1155-1174.

(Continued)

*Primary Examiner* — Scott A. Smith
(74) *Attorney, Agent, or Firm* — Cardica, Inc.

(57) ABSTRACT

A surgical instrument may include a knife moveable from a stowed position completely within said surgical instrument to a cutting position in which at least part of the knife is positioned outside the surgical instrument. The surgical instrument may also include at least two cam slots, a cam pin extending from the knife into the cam slots, at least two guide slots that are substantially linear and are spaced apart from said cam slots, and a guide pin extending from the knife into the guide slots. In some embodiments, the cam slots are shaped to cause the knife to move from the stowed position to the cutting position as the knife is urged proximally.

7 Claims, 3 Drawing Sheets

U.S. PATENT DOCUMENTS

| | | | |
|---|---|---|---|
| 5,620,289 | A | 4/1997 | Curry |
| 5,630,541 | A | 5/1997 | Williamson, IV et al. |
| 5,655,698 | A | 8/1997 | Yoon |
| 5,662,260 | A | 9/1997 | Yoon |
| 5,692,668 | A | 12/1997 | Schulze et al. |
| 5,810,855 | A | 9/1998 | Rayburn et al. |
| 5,816,471 | A | 10/1998 | Plyley et al. |
| 5,855,311 | A | 1/1999 | Hamblin et al. |
| 5,871,135 | A | 2/1999 | Williamson, IV et al. |
| 5,875,538 | A | 3/1999 | Kish et al. |
| 5,894,979 | A | 4/1999 | Powell |
| 5,918,791 | A | 7/1999 | Sorrentino et al. |
| 5,964,774 | A | 10/1999 | McKean et al. |
| 6,306,149 | B1 | 10/2001 | Meade |
| 6,391,038 | B2 | 5/2002 | Vargas et al. |
| 6,419,682 | B1 | 7/2002 | Appleby et al. |
| 6,592,597 | B2 | 7/2003 | Grant et al. |
| 6,602,252 | B2 | 8/2003 | Mollenauer |
| 6,716,232 | B1 | 4/2004 | Vidal et al. |
| 6,817,508 | B1 | 11/2004 | Racenet et al. |
| 6,843,403 | B2 | 1/2005 | Whitman |
| 7,025,747 | B2 | 4/2006 | Smith |
| 7,055,730 | B2 | 6/2006 | Ehrenfels et al. |
| 7,097,089 | B2 | 8/2006 | Marczyk |
| 7,111,768 | B2 | 9/2006 | Cummins et al. |
| 7,128,253 | B2 | 10/2006 | Mastri et al. |
| 7,140,527 | B2 | 11/2006 | Ehrenfels et al. |
| 7,168,604 | B2 | 1/2007 | Milliman et al. |
| 7,172,104 | B2 | 2/2007 | Scirica et al. |
| 7,179,267 | B2 | 2/2007 | Nolan et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,238,195 | B2 | 7/2007 | Viola |
| 7,258,262 | B2 | 8/2007 | Mastri et al. |
| 7,401,720 | B1 | 7/2008 | Durrani |
| 7,434,715 | B2 | 10/2008 | Shelton, IV et al. |
| 7,467,740 | B2 | 12/2008 | Shelton, IV et al. |
| 7,497,865 | B2 | 3/2009 | Willis et al. |
| 7,506,791 | B2 | 3/2009 | Omaits et al. |
| 7,517,356 | B2 | 4/2009 | Heinrich |
| 7,588,177 | B2 | 9/2009 | Racenet |
| 7,604,151 | B2 | 10/2009 | Hess et al. |
| 7,635,073 | B2 | 12/2009 | Heinrich |
| 7,635,373 | B2 | 12/2009 | Ortiz |
| 7,641,093 | B2 * | 1/2010 | Doll et al. ............ 227/175.4 |
| 7,641,432 | B2 | 1/2010 | Lat et al. |
| 7,644,848 | B2 | 1/2010 | Swayze et al. |
| 7,726,537 | B2 * | 6/2010 | Olson et al. ............ 227/175.1 |
| 7,743,960 | B2 * | 6/2010 | Whitman et al. ......... 227/180.1 |
| 7,918,230 | B2 * | 4/2011 | Whitman et al. .......... 128/898 |
| 2003/0120284 | A1 | 6/2003 | Palacios et al. |
| 2003/0236551 | A1 | 12/2003 | Peterson |
| 2005/0184121 | A1 | 8/2005 | Heinrich |
| 2006/0011699 | A1 | 1/2006 | Olson et al. |
| 2006/0041273 | A1 | 2/2006 | Ortiz et al. |
| 2006/0151567 | A1 | 7/2006 | Roy |
| 2006/0253143 | A1 | 11/2006 | Edoga |
| 2007/0027472 | A1 | 2/2007 | Hiles et al. |
| 2007/0034668 | A1 | 2/2007 | Holsten et al. |
| 2007/0073341 | A1 | 3/2007 | Smith et al. |
| 2007/0083234 | A1 | 4/2007 | Shelton, IV et al. |
| 2007/0118163 | A1 | 5/2007 | Boudreaux et al. |
| 2007/0125828 | A1 | 6/2007 | Rethy et al. |
| 2007/0175950 | A1 | 8/2007 | Shelton, IV et al. |
| 2008/0078807 | A1 | 4/2008 | Hess et al. |
| 2008/0272175 | A1 | 11/2008 | Holsten et al. |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology 18*(9), (Nov. 2004),811-817.

Steichen, Felicien M., et al., "Mechanical Sutures in Surgery", *Brit. J. Surg.60*(3), (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

* cited by examiner

CAM-CONTROLLED KNIFE FOR SURGICAL INSTRUMENT

This application claims priority to U.S. Provisional Patent Application Ser. No. 61/175,786, filed on May 5, 2009, which is herein incorporated by reference in its entirety.

FIELD OF THE INVENTION

The invention generally relates to surgical staplers and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter.

In order to overcome these difficulties, Cardica, Inc. of Redwood City, Calif. has developed a true multi-fire endocutter that is capable of firing multiple times without the need to utilize single-use-cartridges. That endocutter is described in, for example, U.S. patent application Ser. No. 12/263,171, filed on Oct. 31, 2008; and U.S. patent application Ser. No. 12/436,101, filed on May 5, 2009 (the "Endocutter Documents"), which are hereby incorporated by reference in their entirety. The Endocutter Documents, among other items, disclose a knife or cutter used to cut tissue before, during and/or after stapling of tissue.

BRIEF DESCRIPTION OF THE DRAWINGS

The use of the same reference symbols in different figures indicates similar or identical items.

DETAILED DESCRIPTION

Figure 1:
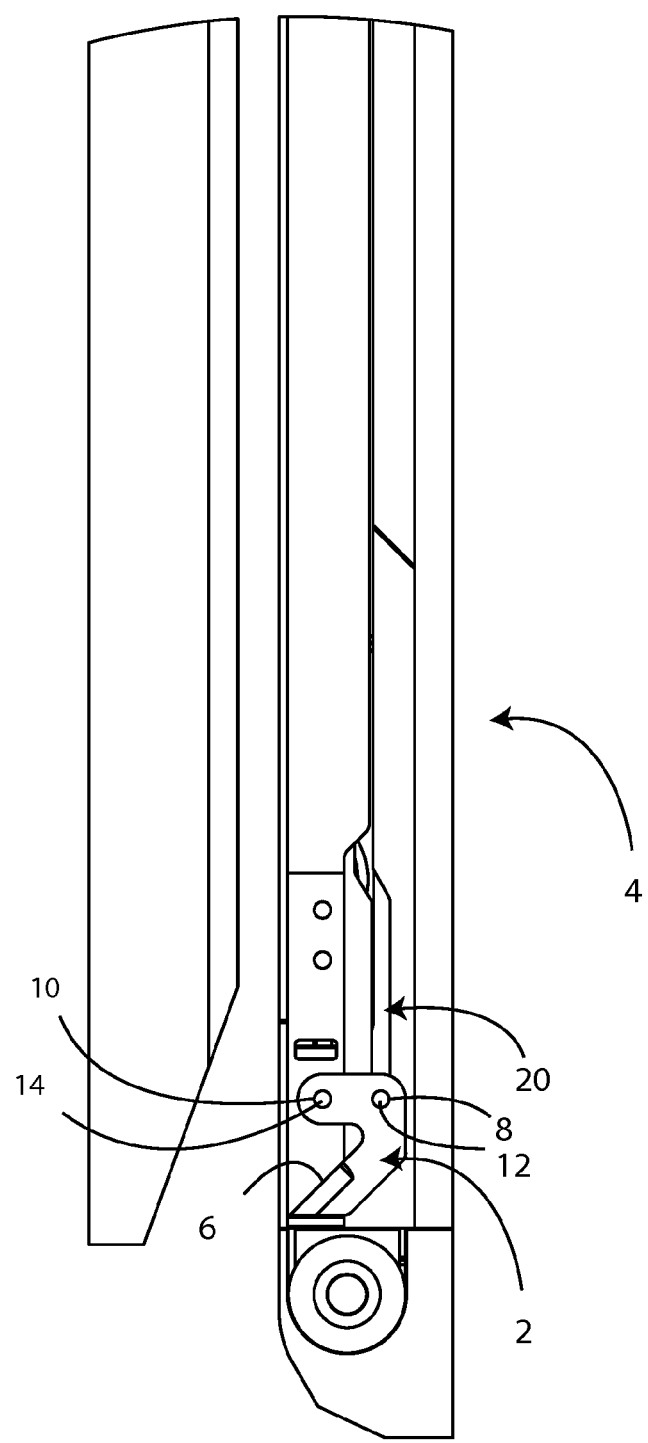
FIG. 1 is a side view of a cam-controlled knife in a first, stowed position in a surgical instrument.

Referring to FIG. 1, a knife 2 is held within a surgical instrument 4 in a first, stowed position. The surgical instrument 4 may be the staple holder of an endocutter such as described in the Endocutter Documents, the anvil or staple holder of an anastomosis stapler such as described in U.S. Pat. No. 7,285,131, which is hereby incorporated by reference in its entirety, or any other suitable surgical instrument. The knife 2 may have a cutting edge 6 that in the first, stowed position is oriented at least partially upward. The knife 2 may include a first aperture 8 and a second aperture 10 located above and spaced apart from the first aperture 8. A first pin 12 may extend into or through the first aperture 8, and a second pin 14 may extend into or through the second aperture 10. Advantageously, the knife 2 is rotatable about the second pin 14. Alternately, the second pin 14 may be fixed to the knife 2. The second pin 14 may extend to and be movable longitudinally by a drive bar or other feature as set forth in the Endocutter Documents. The first pin 12 may simply extend into a cam slot 20 defined in the surgical instrument 4, and thus may be fixed to the knife 2, or rotatable relative to the first aperture 8.

Figure 2:
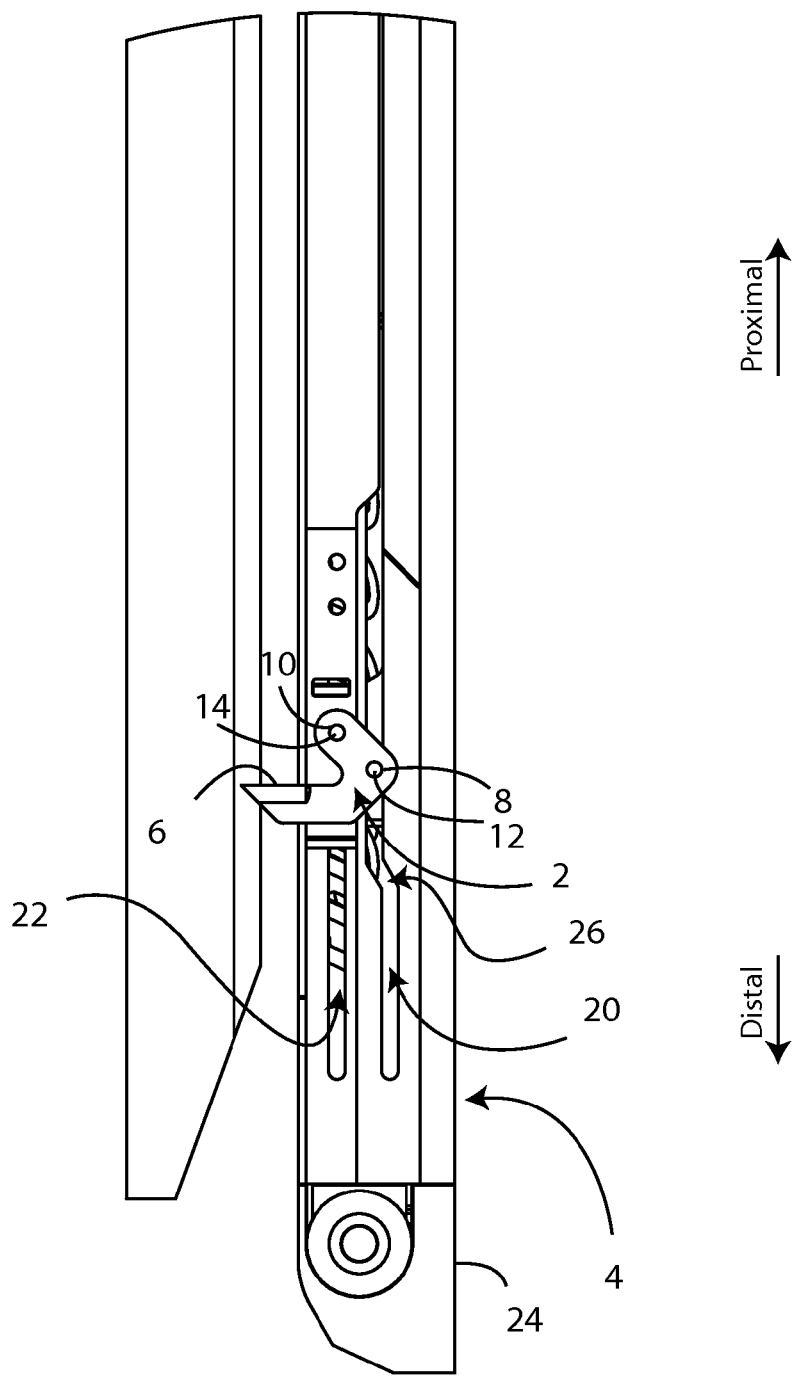
FIG. 2 is a side view of the knife of FIG. 1 in a second, cutting position in a surgical instrument.
Figure 3:
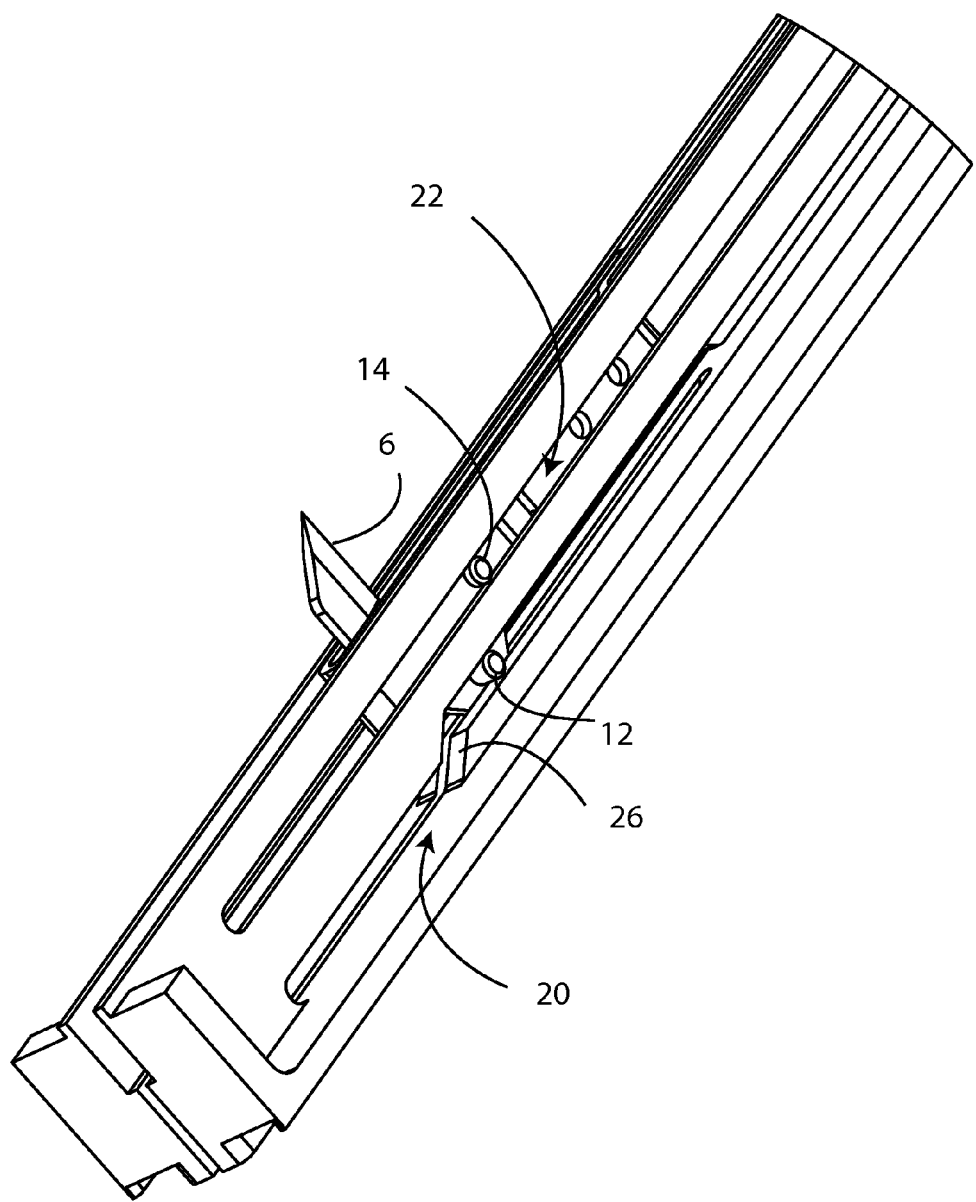
FIG. 3 is a perspective view of the knife of FIG. 1 in the second, cutting position.

The cam slot 20 may have any suitable path for controlling the knife 2. As one example, the distal end of the cam slot 20 may be generally longitudinal, and generally parallel to and spaced a first distance apart from a lower surface 24 of the surgical instrument 4, and the proximal end of the cam slot 20 may be generally longitudinal, and generally parallel to and spaced a second distance apart from a lower surface 24 of the surgical instrument 4, where the second distance is greater than the first distance. Between those ends of the cam slot, a ramp 26 may extend upward in the proximal direction. Alternately, the cam slot 20, rather than being linear, may define a closed two-dimensional path, such that return of the knife 2 to the first, stowed position is accomplished along a different path than the motion of the knife 2 away from the first, stowed position. The second pin 14 may move generally longitudinally along a guide slot 22. As shown in FIGS. 1-3, the guide slot 22 is linear, and thus does not cam the knife 2 relative to the surgical instrument 4. However, the guide slot 22 could be configured to cam the knife 2 relative to the surgical instrument 4, such as by introducing nonlinearity to the guide slot 22, and if so the guide slot 22 may be characterized as a cam slot 20.

The second pin 14 may be pulled longitudinally and proximally along the guide slot 22 during actuation of the surgical instrument 4, such as by a drive bar. As the second pin 14 moves proximally, the first pin 12 follows along in the proximal second of the cam slot 20. When the second pin 14 encounters and runs up the ramp 26, the knife 2 rotates about the second pin 14, due to the decrease in spacing between the guide slot 22 and the cam slot 20. That is, the knife 2 must rotate about the second pin 14 due to the fact that the second pin 14 is constrained to remain in the guide path 22 and the first pin 12 is constrained to remain in the cam path 20. As the knife 2 rotates, the cutting edge 6 moves out of the stowed position, and moves out of the surgical instrument 4 to a second, cutting position. Such motion may cut tissue placed adjacent to the surgical instrument 4. As the second pin 14 continues to be pulled proximally, the cutting edge 6 moves proximally along the surgical instrument 4, incising tissue as it slides. The second pin 14 is moved along the guide path 22 until the travel of the knife 2 is complete. The knife 2 may then be returned to the initial, stowed position simply by reversing the direction of travel of the second pin 14 toward the distal direction.

What is claimed is:
1. Apparatus, comprising:
   a surgical staple holder;
   a knife held by and movable relative to said staple holder, at least in part by rotation, from a stowed position completely within said staple holder to a cutting position in which a cutting edge of said knife is exposed outside said staple holder;

an anvil coupled to said staple holder, wherein said knife is movable upward out of said staple holder and toward said anvil from said stowed position;
at least two cam slots defined in said staple holder; and
at least one pin fixed to said knife that engages the at least two cam slots, wherein each of said cam slots includes two generally-parallel and spaced apart linear segments connected by a ramp segment angled relative to said linear segments, such that contact between said cam pin and each ramp causes upward motion of said knife.

2. Apparatus, comprising:
a surgical instrument;
a knife moveable from a stowed position completely within said surgical instrument to a cutting position in which at least part of said knife is positioned outside said surgical instrument;
at least two cam slots defined in said surgical instrument; a cam pin extending from said knife into said at least two cam slots;
at least two guide slots defined in said surgical instrument, where said guide slots are substantially linear and are spaced apart from said cam slots; and
a guide pin extending from said knife into said at least two guide slots,
wherein said cam slots are shaped to cause said knife to move from said stowed position to said cutting position as said knife is urged proximally, wherein each of said cam slots includes two generally-parallel and spaced apart linear segments connected by a ramp segment angled relative to said linear segments, such that contact between said cam pin and each ramp causes upward motion of said knife.

3. The apparatus of claim 2, wherein proximal motion of said knife causes said cam pin to ride upward on said ramps, thereby causing said guide pin to rotate within said guide slots, wherein said knife rotates upward toward said cutting position.

4. The apparatus of claim 2, wherein said cam slots are shaped to cause said knife to move from said cutting position to said stowed position as said knife is urged distally.

5. Apparatus, comprising:
a surgical knife having a first pin and a second pin extending laterally therefrom;
a cam slot on each lateral side of said knife, wherein said first pin extends into said cam slots;
a guide slot on each lateral side of said knife, wherein said second pin extends into said guide slots; wherein said guide slots are substantially linear and are located above said cam slots;
wherein said knife is slidable in a linear direction substantially parallel to said guide slots, and wherein said guide slots substantially constrain said first pin against motion substantially perpendicular to said linear direction; and
wherein said cam slots are shaped such that sliding of said knife along said linear direction urges said first pin in a direction that has a component of motion substantially perpendicular to said linear direction, and as a result said knife rotates about said second pin.

6. The apparatus of claim 5, wherein the proximal end of each said cam slot is located closer to said guide slot on the same lateral side of said knife than the distal end of each said cam slot.

7. The apparatus of claim 5, wherein each said cam slot includes two generally-parallel and spaced apart linear segments connected by a ramp segment angled relative to said linear segments, wherein the linear segment at the proximal end of each said cam slot is located closer to said guide slot on the same lateral side of said knife than the linear segment at the distal end of each said cam slot.

* * * * *